(12) United States Patent
Hawkins et al.

(10) Patent No.: US 6,959,119 B2
(45) Date of Patent: Oct. 25, 2005

(54) METHOD OF EVALUATING COSMETIC PRODUCTS ON A CONSUMER WITH FUTURE PREDICTIVE TRANSFORMATION

(75) Inventors: Stacy Susan Hawkins, Waldwick, NJ (US); Jeremy James Andrew, Stanney Oaks (GB); Richard Iwao Murahata, Edgewater, NJ (US)

(73) Assignee: Unilever Home & Personal Care USA, Greenwich, CT (US)

( * ) Notice: Subject to any disclaimer, the term of this patent is extended or adjusted under 35 U.S.C. 154(b) by 640 days.

(21) Appl. No.: 09/848,883

(22) Filed: May 4, 2001

(65) Prior Publication Data

US 2002/0054714 A1 May 9, 2002

Related U.S. Application Data

(60) Provisional application No. 60/245,507, filed on Nov. 3, 2000.

(51) Int. Cl.$^7$ .................................................. G06T 3/00
(52) U.S. Cl. ........................ 382/276; 382/115; 382/307; 382/308
(58) Field of Search ................................ 382/276, 115, 382/307, 308

(56) References Cited

U.S. PATENT DOCUMENTS

| | | | |
|---|---|---|---|
| 4,276,570 A | | 6/1981 | Burson et al. ............... 358/903 |
| 5,163,010 A | | 11/1992 | Klein et al. .................. 364/479 |
| 5,291,889 A | * | 3/1994 | Kenet et al. ................. 600/425 |
| 5,990,901 A | * | 11/1999 | Lawton et al. ............... 345/581 |
| 6,215,893 B1 | * | 4/2001 | Leshem et al. ............. 382/128 |
| 6,502,583 B1 | * | 1/2003 | Utsugi ........................ 132/200 |
| 6,571,003 B1 | * | 5/2003 | Hillebrand et al. ......... 382/118 |

FOREIGN PATENT DOCUMENTS

| | | | | |
|---|---|---|---|---|
| FR | 2728982 | | 12/1994 | ........... G06F/17/00 |
| JP | 63006461 | | 1/1988 | .......... G01N/33/48 |
| JP | 05196436 | | 8/1993 | ........... G01B/11/24 |
| JP | 07100126 | | 4/1995 | ........... A61B/5/107 |
| JP | 08299288 | | 11/1996 | ............ A61B/5/00 |
| JP | 11143352 A | * | 5/1999 | ............ G09B/9/00 |
| WO | 97/29441 | | 8/1997 | ........... G06F/17/60 |
| WO | WO 01/82154 | | 11/2000 | ........... G06F/17/60 |

OTHER PUBLICATIONS

Hawkins SS, Perrett DI, Burt DM, Rowland DA and Murahata RI. "Prototypes of facial attributes developed through image averaging techniques", Intern. J. of Cos. Science, 21;159–166 (1991).

Rowland DA, Perrett DI, Burt DM, Lee KJ and Akamatsu S. "Transforming Facial Images in 2 and 3–D", Imagina 97–Conferences–Actes/Proceedings, pp. 1–8, Feb. 1997.

Burt DM, Perrett DI. "Perceptual asymmetries in judgments of facial attractiveness, age, gender, speech and expression" Neuropsychologia 35(5):685–693, 1997.

Burt DM, Perrett DI. "Perception of age in adult Caucasian male faces: computer graphic manipulation of shape and colour information." Proc. R. Soc. Lond. B 259:137–143, 1995.

Rowland DA, Perrett DI. "Manipulating facial appearance through shape and color." IEEE Computer Graphics and Applications 15(5):70–76, 1995.

Perrett DI, May KA, Yoshikawa S. "Facial shape and judgments of female attractiveness." Nature 368:239–242, 1994.

Nobori et al. "Image Synthesis System Using 3D Model-based Coding—Simulates Facial Expressions And Aging", Consumer Electronics, 1992, Digest of Technical Papers, ICCE, IEEE 1992 International Conference on Rosemont, IL, USA Jun. 2–4, 1992, NY, NY USA, IEEE, US Jun. 2, 1992, pp. 394–395.

Yin Wu Pierre Beylot Magnenat Thalmann et al, "Skin aging estimation by facial simulation" Computer Animation, 1999, Proceedings Geneva, Switzerland May 26–29, 1999, Los Alamitos, CA USA, IEEE Comput. Soc., US May 26, 1999, pp. 210–219, XP–010343904.

Wu et al. "A Dynamic Wrinkle Model in Facial Animation and Skin Ageing", Journal of Visualization and Computer Animation, vol. 6, No. 4, 1995, pp. 195–205, XP–000922853.

* cited by examiner

*Primary Examiner*—Leo Boudreau
*Assistant Examiner*—Dennis Rosario-Vasquez
(74) *Attorney, Agent, or Firm*—Milton L. Honig

(57) ABSTRACT

A method kit is provided for demonstrating the effects of a cosmetic product on a consumer's body, especially effects over a period of time. The method includes applying a cosmetic product to the body, capturing an image of the consumer, displaying the image on a monitor and digitally transforming the image to reflect the effect of using the selected cosmetic over the period of time. Among transformed attributes of the body are those of glow/color, sags/wrinkles, pores and combinations thereof. The original and transformed images are juxtaposed on a screen. Consumers are required to select between transformed and displayed images, preferably repetitively, until the consumer has chosen their most appealing transformation.

2 Claims, No Drawings

METHOD OF EVALUATING COSMETIC PRODUCTS ON A CONSUMER WITH FUTURE PREDICTIVE TRANSFORMATION

CROSS REFERENCES

This application claims priority benefit from Provisional Application Ser. No. 60/245,507 filed Nov. 3, 2000.

BACKGROUND OF THE INVENTION

1. Field of the Invention

The invention concerns a method for transforming an image of a consumer's skin, especially facial skin, to an image with a consumer-defined composite cosmetic attribute.

2. The Related Art

Cosmetic companies have developed on-counter visualization tools to show wrinkles and how they can worsen, based on increasing the length and width of the wrinkles. These tools are not based on actual consumer or clinical data, or actual studies of the progression of a wrinkle over time. In addition, many companies have the technology to display actual images with color changes to the face, without showing how the face would appear as a result of improving a consumer-defined composite cosmetic attribute. See for instance JP 7100126 and JP 5196436 (Shiseido). Another patent from Shiseido (JP 63006461) provides recommendations from a video editing system based on the roughness of a replica taken on counter. JP 8299288 (Kanebo) describes "spot" measurements, which may be related to dryness, oiliness, or color over a small (mm size) region on the skin. While these measurements are on-counter diagnostics, they do not include an overall attribute visualization of the face as in the present invention.

Clinique has a web site for product recommendation, based on user input. It does not involve actual changes or expert ratings in any composite cosmetic attribute or healthy skin. Revlon in U.S. Pat. No. 5,163,010 describes a similar system for recommending custom mixed products based on surveys at the point of sale.

Studies exist on the relationship of facial features to the perception of age and gender. See for instance Hawkins S S, Perrett D I, Burt D M, Rowland D A and Murahata R I. "Prototypes of facial attributes developed through image averaging techniques", Intern. J. of Cos. Science, 21; 159–166 (1991); Rowland D A, Perrett D I, Burt D M, Lee K J and Akamatsu S. "Transforming Facial Images in 2 and 3-D", Imagina 97-Conferences-Actes/Proceedings, Pages 1–8, February 1997; Burt D M, Perrett D I. "Perceptual asymmetries in judgments of facial attractiveness, age, gender, speech and expression" Neuropsychologia 35(5):685–693, 1997; Burt D M, Perrett D I. "Perception of age in adult Caucasian male faces: computer graphic manipulation of shape and colour information." Proc. R. Soc. Lond. B 259:137–143, 1995; Rowland D A, Perrett D I. "Manipulating facial appearance through shape and color." IEEE Computer Graphics and Applications 15(5):70–76, 1995; Perrett D I, May K A, Yoshikawa S. "Facial shape and judgments of female attractiveness." Nature 368:239–242, 1994. These articles have advanced imaging technology but have not been applied specifically to model individual attributes, which taken collectively define a composite cosmetic attribute (e.g., "healthy" skin), sought by a consumer.

Accordingly, it is an object of the present invention to provide a method for presenting an image of a consumer's skin, especially that of the face, in a manner reflecting a cosmetic product's effect over a period of time.

Another object of the present invention is to provide a method for evaluating a cosmetic product on a consumer's face or other body parts through image transformation over a period of time.

Still another object of the present invention is to provide a method wherein an image of an individual's actual face is transformed over time and the effects of a cosmetic product on color, sags, wrinkles, texture and radiance can be demonstrated.

Yet another object of the present invention is to provide a method for demonstrating to a potential customer the benefit of certain cosmetic products when used over a period of time and allowing comparison with the effects of non-treatment.

These and other objects of the present invention will become more fully apparent from consideration of the following summary and detailed discussion.

SUMMARY OF THE INVENTION

A method is provided for demonstrating effectiveness of a cosmetic product on a consumer's body parts when applied over a period of time, the method including:
 (i) selecting a cosmetic product for trial on the consumer's body and identifying a body feature being observed over the time;
 (ii) capturing an image of the body part;
 (iii) displaying the image on a monitor;
 (iv) digitally transforming the selected body feature on the displayed image in conformance with a predicted effect of the cosmetic product and displaying the digitally transformed image;
 (v) allowing the consumer to compare results of the transformed versus the displayed image; and
 (vi) optionally repeating steps (iv) and (v) till the consumer has chosen an optimal transformation.

Among the body features which may be manipulated are those of texture (pores), sags/lines/wrinkles and radiance/color. In most instances the body part selected for transformation will be that of the face or portions of the face. Comparison of images in step (v) may be tiled on the same screen. Alternatively the displayed and transformed images may be on separate screens. They may also be viewable on consecutive screens, usually by a single click of a computer mouse or key. The tile option is preferred. This mode may also include having more than one transformed image placed on a screen with the original displayed image. For instance, three transformed images can be placed adjacent to a displayed image wherein each of the transformed images represents the effects of using a particular cosmetic product over one month, two months and one year.

The present invention is also concerned with a method for identifying cosmetic needs of a consumer with respect to physical changes that are personal to the consumer, the method including:
 (i) gathering information from the consumer concerning the consumer's cosmetic needs in treating a body feature;
 (ii) capturing an image of the consumer's body feature;
 (iii) displaying the image on a monitor;
 (iv) digitally transforming in a manner reflecting the effect of a recommended cosmetic over a period of time on a property of the body feature selected from color, sags, wrinkles, texture, radiance and combinations thereof, and displaying the transformed image;
 (v) requiring the consumer to select between transformed and displayed images; and (vi) optionally repeating steps (iv) and (v) till the consumer chooses an optimal transformation.

A further aspect of the invention is a kit for displaying a consumer's skin image on a computer screen and transforming the image into consumer-defined composite attributes. Included is a camera for obtaining a high resolution image of the consumer's skin or hair, and a programmable device for receiving the image, transforming the image to an optimum image by subtracting from or adding to the image a number of difference images constructed from prototypes for each attribute of a composite cosmetic attribute.

In a preferred embodiment, the programmable device also evaluates the direction and amount of the change for each attribute of the composite cosmetic attribute, so that a skin cosmetic product or regimen can be recommended to a consumer. Recommendation may also be done by a programmable device.

When the method focuses upon aging attributes, improvement from one image to another can be expressed as a percentage improvement. According to the present invention, it is possible to replace the percentage concept simply with a value of number of years reduction in apparent appearance.

The invention employs a method for obtaining a transform of a composite cosmetic attribute, the method including:

(a) identifying, preferably via a consumer study, individual attributes of a composite cosmetic attribute and grading a plurality of subjects on each attribute;

(b) computing an average for subjects rated low and an average for subjects rated high to obtain the high prototype and the low prototype for each attribute;

(c) computing a difference image for the individual attribute between a high and a low prototype;

(d) obtaining an optimum image by subtracting from or adding to an actual captured image increments of the difference image.

Preferably, an optimum image is obtained by simultaneously subtracting/adding difference images for several or all attributes that are identified. Thus the captured image is transformed by a consumer to an optimum image with a composite cosmetic attribute, to a degree desired by a consumer. The inventive device and method allow consumers to regulate the degree to which they adjust each component of a composite cosmetic attribute. In the most preferred embodiment of the invention, the method is consumer-driven: first, the composite cosmetic attribute is defined by a consumer (preferably, by a large consumer panel); then prototypes are obtained from consumer gradings (preferably, expert panel grading of a large number of consumers), and finally a consumer defines her/his image with a composite cosmetic attribute, being able to adjust each individual component of a composite cosmetic attribute.

In the preferred embodiment of the invention, the transformed image defined by a consumer is subsequently analyzed by a cosmetics manufacturer (or a sales representative) to evaluate the amount and direction of the change for each attribute of the composite cosmetic attribute. Subsequently, a cosmetics manufacturer (or sales representative thereof) can recommend a skin cosmetic product or a skin cosmetic regimen which would assist the consumer in attaining the transformed image.

The inventive method and kit are capable of displaying a transformed image which contains an attribute not at all present in the captured image. For instance, a consumer may see glow in the transformed image, even if there was no glow at all in the captured image.

Yet a further aspect of the present invention involves a method for identifying progress in the affect of an applied cosmetic product upon a consumer which affect is personal to that consumer, the method including:

(i) selecting a cosmetic product for trial on the consumer's body and identifying a body feature being observed over a period of time;

(ii) capturing an image of the body feature;

(iii) displaying the image on a monitor;

(iv) capturing a further image of the body feature at a later time after the product has been applied by the consumer;

(v) allowing the consumer to compare results between the captured and later time captured images; and (vi) optionally digitally transforming the captured image of step (ii) in conformance with a predicted affect of the cosmetic product and displaying the digitally transformed image thereby allowing comparison to the later time captured image representing an actual cosmetic product treated body feature as obtained from step (iv).

DETAILED DESCRIPTION OF THE INVENTION

Now it has been found that a consumer's actual face or other body part can be digitally transformed through a computer program to demonstrate effects of a cosmetic product treatment. The treatment may simply be an application of different colors onto skin (such as evaluating the different shades of lipstick, blush, eye or lip liners, foundation and mascara) or even hair. The latter may include coloring, hair growth or even depilatation. Transformations of the present invention take into account not only topography and shape of a face but also its color and texture. An important aspect of the invention is that transformed and originally displayed images are placed either beside one another or on adjoining screen views. The consumer is forced to pick between two of the images. Forced choice ordinarily is between a transformed and an original displayed image but may also occur between different ones of the transformed images.

According to the present invention a consumer is assisted in evaluating cosmetic products with a future predictive transformation obtainable in the following manner. High resolution images are captured of body sites which may benefit from the cosmetic products. Feature points are then semi-automatically delineated along the skin surface of those sites. Images have been grouped by one or more of a series of attribute scales to define an Attribute S.

Based on consumer perception studies, it was determined that female consumers wanted healthy looking skin. "Healthy" skin is a composite cosmetic attribute, which has not been previously defined. The term "skin" as used herein includes skin on the face, neck, hands, chest, arms and legs. Attribute S was developed using a set of scales to define healthy skin.

Qualitative language generation with Caucasian females in the US was performed to determine the individual attributes of healthy looking facial skin, and expert graders were trained based on the consumer language.

The study classified various cosmetic facial attributes as consumer-perceivable attributes that contribute to the overall appearance of cosmetic health. Typical attributes included lines and wrinkles, pores, blemishes, softness, silkiness and glow/color. Thus, the individual indicia of healthy facial skin were defined objectively and by a consumer.

Three attributes (glow/color, lines and wrinkles, and pores) were then worked on as follows: Expert evaluations and photographs were taken of 80 panelists with no treatment/product use. The panelists all wore white hair caps, black bibs, and had cleansed their faces with their normal cleansing products 2 hours prior to their arrival at the study site. The photographs were recorded to PhotoCD for processing. From these images, facial averages were computed for panelists with the 9 lowest ratings for healthy glow/color, and the highest ratings for lines and wrinkles, and pores. The methods for computing facial averages have been previously described in the literature. These facial averages, or prototypes, provided insight into the primary regions of interest for each of the three attributes. Difference images were than constructed by subtracting the low prototype from the high prototype. This procedure was repeated for 19 attributes total, which together defined a composite cosmetic attribute "healthy skin."

Novice graders were prompted to "make faces look healthy," using varying percentages of difference images to apply a positive or negative transform of a particular attribute. Subjects were shown 9 faces in each of the three attribute categories (glow/color, pores, and lines and wrinkles). The transforms were shown in random order with counterbalanced directions of transforms and mid-range points. Three faces were rated high, three mid-range, and three low for each category by expert graders. It was confirmed that novice graders were able to describe what they were seeing in the process of transforming the image and that their description corresponded well to the attributes developed by expert graders. Known physiological processes were detected on individual attributes, e.g. aging for lines/wrinkles.

The novice graders recognized all of the transforms as changing perceived facial health in the transformed attribute along the correct transform direction. For example, subtraction of an attribute resulted in a decreased perception of healthy glow, pores, or lines and wrinkles.

The same experiment performed with novice graders was repeated with panel experts. Expert graders were able to identify the attribute that was used in obtaining a transformed image. Like novice graders, expert graders were able to identify the correct direction for an attribute resulting in a transformed image.

According to the present invention, a consumer has their picture taken at a sales counter. By adjusting the captured image through varying amounts and directions of difference images, an operator obtains a consumer's definition of their own ideal healthy skin. Customized product information can then be given to the consumer at the counter to help achieve this ideal. Clinically proven changes in products could also be shown to the consumer on their own image using this point of purchase interactive imaging system. Instead of a retail counter, the whole process may be conducted from a consumer's home via Internet transmissions and by use of a consumer's own digital camera.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method for identifying progress of a cosmetic product treatment affect upon a consumer, the affect being personal to that consumer, the method comprising:
   (i) selecting a cosmetic product for trial on the consumer's body and identifying a body feature being observed over a period of time;
   (ii) capturing an initial image of the body feature;
   (iii) displaying the initial image on a monitor;
   (iv) providing an assessment of the initial image based on results of an expert grader study which has calculated consumer perceivable skin attributes on panelists with no treatment/product use;
   (v) digitally transforming in a manner reflecting the effect of a recommended cosmetic over a period of time, based upon the assessment, of a property of the body feature of the consumer selected from color, sags, wrinkles, texture, radiance and combinations thereof, and displaying the transformed image tiled beside the initial image;
   (vi) capturing a further image of the body feature at a later time after the product has been applied by the consumer;
   (vii) allowing the consumer to compare results between the captured initial, digitally transformed, and later time captured images.

2. The method according to claim 1 wherein capturing step (ii) is performed by use of a digital camera and wherein the captured image is transmitted via Internet.

* * * * *